United States Patent [19]

Yamamoto et al.

[11] 4,237,959
[45] Dec. 9, 1980

[54] METHOD OF EXAMINING THE SURFACE OF A CONTINUOUSLY CAST METAL STRIP FOR DETECTION OF SCARFS APPEARING THEREON AND APPARATUS FOR THE SAME

[75] Inventors: Tomio Yamamoto; Hideyuki Hanafusa; Kouji Seno, all of Takamatsu; Toshiro Mihara, Tokyo; Isoshiro Ishida, Machida, all of Japan

[73] Assignee: Futec Inc., Takamatsu, Japan

[21] Appl. No.: 22,372

[22] Filed: Mar. 20, 1979

[30] Foreign Application Priority Data

Mar. 23, 1978 [JP] Japan .................................. 53-33312
Mar. 23, 1978 [JP] Japan .................................. 53-33313

[51] Int. Cl.$^3$ .............................................. B22D 2/00
[52] U.S. Cl. ........................................ 164/4; 164/150
[58] Field of Search .................... 164/4, 150, 154, 82; 356/237; 358/106, 107; 264/40.1

[56] References Cited

U.S. PATENT DOCUMENTS

| 4,118,732 | 10/1978 | Ichijima et al. | 358/106 |
| 4,131,490 | 12/1978 | Oishi et al. | 358/106 |

FOREIGN PATENT DOCUMENTS 43-14102  6/1968  Japan .................................. 356/237

OTHER PUBLICATIONS

"High-Speed Automatic Particle Counter" by Shaw et al., IBM Technical Disclosure Bulletin, vol. 17, No. 9, 2/75.

*Primary Examiner*—Robert D. Baldwin
*Assistant Examiner*—K. Y. Lin
*Attorney, Agent, or Firm*—Frishauf, Holtz, Goodman & Woodward

[57] ABSTRACT

A method and apparatus for examining the surface condition of a traveling metal strip in the process of being continuously cast for detection of scarfs, if any, produced on said surface, wherein a light emitter projects light beams of short waves or those containing said short waves and other waves on a traveling metal strip in the process of being continuously cast; among the reflections of the projected light beams, only those consisting of short waves are received by the light detector through a filter; a flat hood surrounding a light path extending between the light emitter and light detector is set in a cooling chamber; compressed air streams run through the flat hood to air purge or clean the environment of the light path; a signal issued from the light detector is processed by an image memory; the shade image of the traveling metal strip is continuously displayed on the screen of a monitor television set; and the surface condition of the traveling metal strip is examined on the screen to detect scarfs, if any, produced on said surface.

12 Claims, 6 Drawing Figures

METHOD OF EXAMINING THE SURFACE OF A CONTINUOUSLY CAST METAL STRIP FOR DETECTION OF SCARFS APPEARING THEREON AND APPARATUS FOR THE SAME

BACKGROUND OF THE INVENTION

This invention relates to a method of detecting scarfs appearing on the surface of continuously cast steel strip such as a slab or billet, while they remain hot, by means of a remote contactless process.

A continuous casting method has recently achieved a prominent progress as a substitution for the known blooming process. In this case, the customary practice of detecting scarfs occurring on the surface of a steel strip in the process of being continuously cast is to cool the strip to room temperature and examine the surface by the naked eye or any other unreliable means to find scarfs, if any, appearing thereon. Consequently, such prior art examination process has the drawbacks that the examination step consumes a long time, and leads to the possibility of disqualified product being manufactured with the resultant decline in the yield; and, if scarfs are detected by examination, the product has to be heated again after removing the scarfs, thus resulting in considerable heat loss.

Another examination method known to date is to observe the surface of a hot steel strip in the process of being continuously cast, with notice taken of the fact that the steel strip travels at a lower speed than in the blooming method. However, this proposed examination method has been little put into practice because of the drawbacks that since an examination operator can not approach a hot steel strip, the examination step is accompanied with considerable difficulties and risks and has low reliability.

No apparatus has yet been developed which examines the surface of a steel strip in the process of being continuously cast for detection of scarfs appearing thereon in any desired spot, for example, in a cooling chamber in which a large number of support rollers are horizontally arranged. Hitherto, examination has generally been undertaken in a shop where a plurality of withdrawal rollers or straightening rollers are set. The reason is that examination in the cooling region is encountered with great difficulties due to the ejection of large volumes of cooling water from a series of sprays and the resultant generation of steam.

Where, however, a steel strip in the process of being continuously cast happens to indicate such a defective surface condition as demands an instant care, it is preferred to detect such defect as soon as possible, supply data on the result of said detection to, for example, a control section for adjusting the casting rate, and to take early countermeasures such as adjustment of the casting rate of a steel strip which constitutes at least one of the main causes leading to the growth of scarfs. To date, however, no apparatus has been known which meets the above-mentioned requirements, relative to the continuous casting of a steel strip.

It is accordingly the object of this invention to provide a compact apparatus and an effective method for accurately and sufficiently detecting scarfs appearing on the surface of a steel strip such as a slab or billet in the process of being continuously cast at any desired spot, or preferably in a cooling chamber substantially without being affected by cooling water or steam.

SUMMARY OF THE INVENTION

To attain the above-mentioned object, this invention provides an apparatus for examining the surface of a steel strip in the process of being continuously cast which comprises a light emitter provided with a light source issuing light beams consisting of wavelengths falling within the range of short waves and other waves, the light beams being projected onto the metal strip; a light detector provided with a filter which passes light beams having only short wavelengths, the light detector receiving light reflected from the metal strip; a flat hood surrounding the light path extending between the light emitter and light detector; and an image memory device supplied with an electrical signal representing the shadow of a steel strip in the process of being continuously cast which is brought into the light detector when the environment of said light path is purged by compressed air entering the hood, and wherein, after processing by the image memory, the shadow of the steel strip is continuously projected on a monitor television set, thereby detecting scarfs, if any, appearing on the surface of the steel strip. The main part of a strip surface-examining apparatus embodying this invention is set, preferably, in a cooling chamber of the continuous casting apparatus. The outer end of the flat hood is located between two adjacent support rollers to face a steel strip being in the process of being continuously cast.

The strip surface-examining apparatus of this invention arranged as described above accurately indicates the surface condition of a steel strip in the process of being continuously cast even in a cooling chamber substantially without being affected by cooling water and steam, and further enables a broad area of the surface of said steel strip to be continuously observed on a monitor television set. Moreover, the surface condition of the steel strip is examined in the initial stage of its travel, making it possible to resolve causes leading to the occurrence of scarfs on the surface of the steel strip quickly by supplying data on the result of examination to a control section to adjust the casting rate of the steel strip. The strip surface-examining apparatus of the invention is made compact and thus allows for the examination of the surface of a steel strip in the process of being continuously cast. Since the hood of the apparatus is made flat, full examination can be carried out even through a space between a large number of closely arranged rollers. Further, the apparatus of the invention is saved from thermal shocks by replacement of the detachably constructed head of the air purge hood. The opening of the head is provided with means for preventing its thermal deformation, rendering the head very durable.

DETAILED DESCRIPTION

Figure 1:
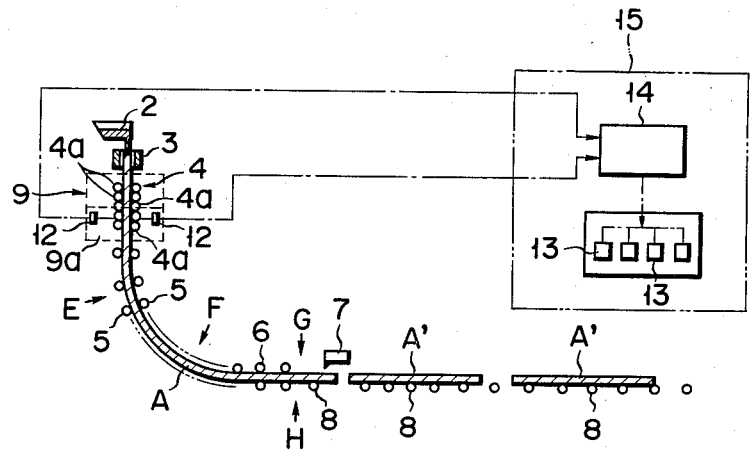
FIG. 1 schematically shows the arrangement of a continuous casting plant provided with the apparatus of this invention for examining the surface condition of a steel strip in the process of being continuously cast.

FIG. 1 schematically indicates the arrangement of a curved strip type continuous casting plant. A casting mold 3 is set near the outlet of a tundish 2 for receiving molten steel from a ladle. Disposed on the outlet side of the mold 3 are a large number of rollers 4a arranged in two parallel rows and a spray assembly 4 consisting of spray nozzles facing the respective rollers 4a. Withdrawal rollers 5 and straightening rollers 6 are arranged on that side of the spray assembly 4 from which a steel strip in the process of being continuously cast is drawn forward. Provided further ahead of the spray assembly 4 is a gas cutter 7.

A cast slab A' cut off by the gas cutter 7 is brought to the succeeding rolling step by means of table rollers 8. With this continuous casting plant 1, the mold 3 defines the shape of the slab A being continuously cast, and draws off the slab A downward by reciprocated vertical movement. The spray assembly 4 guides the slab A while preventing it from being deformed, and cools it by spraying water thereon through a space between the respective rollers 4a. The spray assembly 4 is received in a cooling chamber 9 consisting of two upper and lower compartments. The linearly arranged rollers 4a constituting each of the two parallel rows are spaced from each other at a distance of, for example, about 20 mm to about 100 mm. The slab A leaving the spray assembly 4 is drawn down by withdrawal rollers 5 while being allowed to cool naturally, and straightened by straightening rollers 6, and finally cut to a prescribed length by the gas cutter 7. The adjacent withdrawal rollers 5 arranged on either side of the slab A are spaced from each other at a progressively greater distance, as they are drawn nearer to the gas cutter 7. Generally, the withdrawal rollers 5 are properly spaced from each other at a distance falling within the range of 200 to 300 mm. The slab A travels at a speed as low as 1 to 2 m/min and is kept at as high a temperature as several hundreds of degrees centrigrade (for example, higher than 600° C.), and of course still remains in the so-called red-hot state.

The main section of the strip surface-examining apparatus of this invention is installed, as shown in FIG. 1, in the lower compartment 9a of the cooling chamber 9. While being operated, the cooling chamber 9 is indeed filled with a mixture of cooling water ejected from the spray assembly 4 and steam resulting from contact between said cooling water and a molten steel strip, thus producing a very hot region which is extremely difficult to observe. This objectionable condition is easily eliminated, as later described, by a special device included in the strip surface-examining apparatus of this invention.

There will now be described by reference to FIG. 2 the arrangement and operation of the strip surface-examining apparatus of this invention. Fundamentally, this apparatus comprises a light emitter 10 for sending forth narrow light beams across the surface of a slab A in the process of being continuously cast; a light detector 11 for receiving reflections of the emitted light beams and producing a shade image of the slab surface; an air purge device 12 for cleaning the environment of the light paths of the light emitter 10 and light detector 11; and an image memory 14 (FIG. 1) for continuously projecting an image on a monitor television set 13 (FIG. 1) upon receipt of signals from the light detector 11. The light emitter 10, light detector 11 and air purge device 12 jointly constituting the main section of the strip surface-examining apparatus of this invention are set, as shown in FIG. 1, in the lower compartment 9a of the cooling chamber 9. The image memory 14 and electric equipment including the monitor television set 13 also included in the subject strip surface-examining apparatus are received in an operation room 15 (FIG. 1) set apart from a continuous casting plant 1. The cleaning of the environment of the light emitter 10 and light detector 11 by the air purge device 12 means that, as detailed later, while the continuous casting plant 1 is in operation, compressed air streams are passed through the light path to eliminate cooling water, steam, scales falling off a steel strip, dust and other foreign matter from said light path, thereby increasing the reliability of the examination of the surface of a steel strip in the process of being continuously cast. In a preferred embodiment, air streams are introduced into the region of the light path at a pressure of substantially 5 atmospheres.

Figure 2:
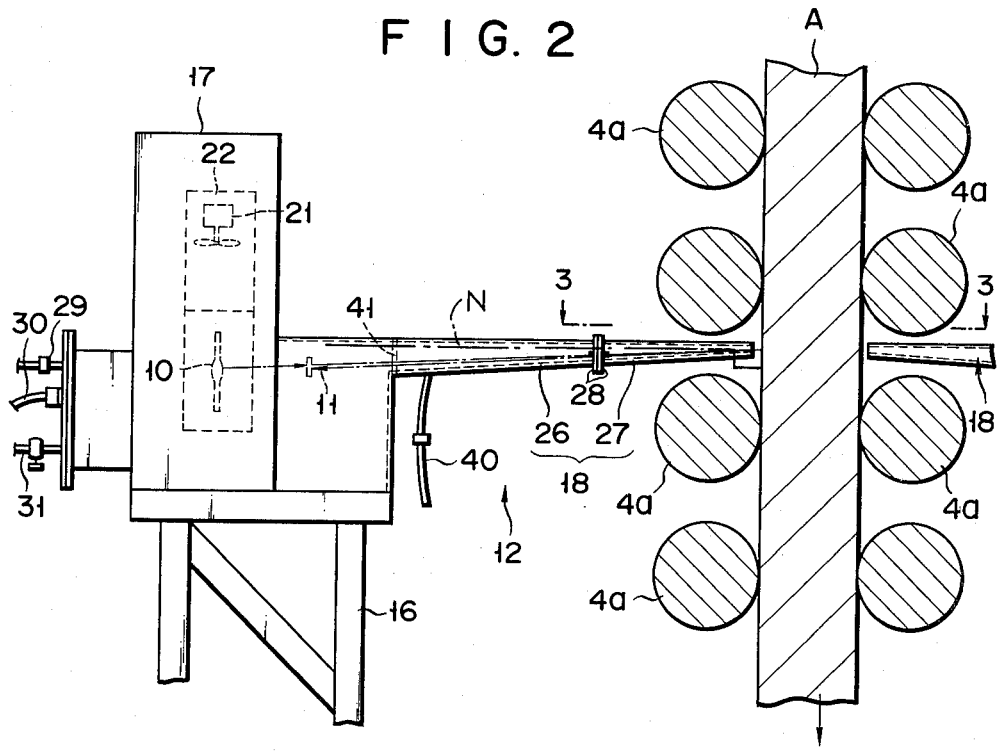
FIG. 2 is an enlarged view of the strip surface-examining apparatus of the invention set in the lower chamber of the continuous casting plant of FIG. 1.

The light emitter 10 couples a prescribed position as shown in FIG. 2, to project light beams on the slab A in a direction slightly inclined to a normal (line N) in order to provide an image having a good contrast, thereby facilitating the detection of scarfs appearing on the surface of the slab A. The light detector 11 which is set at a point falling slightly outside of the path through which light beams sent forth from the light emitter 10 travel after being reflected from the surface of the slab A is adapted to provide an image with proper contrast.

The housing 17 of the subject strip surface-examining apparatus and a flat air purge hood 18 connected to one lateral wall of said housing 17 are mounted on a stand 16 built in the lower compartment 9a of the cooling chamber 9. As seen from FIG. 3, the housing 17 contains the light emitter 10 consisting of a light source 19 and light-emitting lens 20 (FIG. 3) and also a light source shield 22 which is used to prevent dust from being deposited on the light source 19, and in which a cooling fan 21 (FIG. 2) is provided. The cooling fan 21 maintains the ambient temperature of the light source 19 at such a level as allows for its proper operation, thereby saving the thermal destruction of, for example, the mouthpiece of the light source 19. The light source 19 is of the type which emits blue light beams having such short wavelengths as overcome those of red light beams issued from the hot slab A or another type which sends forth light beams including said blue light beams. It is practically possible to use, for example, a high pressure mercury lamp, ultrahigh pressure mercury lamps, or a Xenon lamp. It is particularly preferred to use the ultrahigh pressure mercury lamp. An ultrahigh pressure mercury lamp, if used, is chosen to have short wave lengths falling within the range of 250 to 550 nanometers (hereinafter abbreviated as "nm"). Short wavelengths in actual use consist of any of the main line spectral portions of 365 nm, 405 nm and 436 nm or a mixture thereof. The reason is that if light beams issued from the ultrahigh pressure mercury lamp contain those having longer wavelengths than 550 nm, then difficulties will arise in distinguishing between said light beams from said mercury lamp and those emitted from a red-hot slab; and at shorter wavelengths than 250 nm, the ultrahigh pressure mercury lamp fails to function properly. For the object of this invention, the light emitting lens 20 is made cylindrical. Consequently, light beams are sent forth from the light source 19 across a slab A in the narrow intense form. Generally as seen from FIG. 3, the light emitters 10 are provided in pairs in the housing 17. Light beams given off from these paired light emitters 10 are made to converge at a certain point on the surface of the slab A. However, one of these paired light emitters 10 is generally preserved as a spare. The light emitter 10, light source shield 22 and cooling fan 21 are supported by proper means (not shown) in the housing 17.

Figure 3:
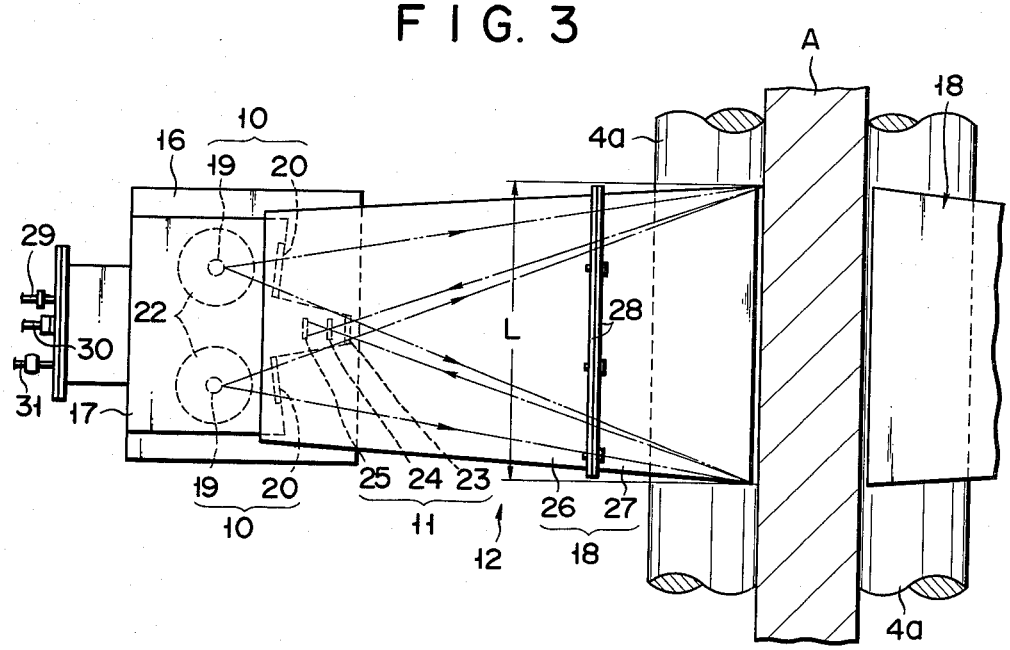
FIG. 3 is a top view of the whole apparatus of FIG. 2, with the portion designated by line 3—3 of FIG. 2 being shown in section.

As shown in FIG. 3, the light detector 11 is formed of a filter 23, lens 24, and image pickup 25. Among reflections from the surface of the slab A, the image pickup 25 detects only blue light beams originally issued from, for example, the ultrahigh pressure mercury lamp, and is supported in the housing 17 by proper means. The filter 23 concurrently acts as means for preventing dust from being deposited on the lens 24 and image pickup 25, and is fitted to an opening formed in one of the lateral walls of the housing 17. The filter 23 is, for example, a band pass filter or interference filter which cuts off red light beams. For the object of the invention, the image pickup 25 may consist of a television camera, linear array image sensor or aerial type image sensor. Particularly preferred, however, is a linear array image sensor. This linear array image sensor is of the known type diversely referred to as a linear array, linear array photodiode, image sensor, line sensor, solid scanner or C.C.D. element. The image pickup 25 consists of a required number of light detecting elements which are designed to convert light beams into electric signals and arranged at a pitch of scores of microns. The foregoing embodiment uses a linear array image sensor of the 512-bit type.

The air purge hood 18 is made flat and constitutes an air purge device 12 together with, for example, an air compressor (not shown). Compressed air is conducted into the air purge hood 18 from said air compressor through an air pipe 40 (FIG. 2). The air purge hood 18 consists of a hood body 26 supported on the stand 16 and an air purge head 27 flange-connected to the forward end of the hood body 26 in a sealed state preferably with a heat-insulating material interposed. Light beams issued from the light emitter 10 and reflections thereof are conducted through the air purge hood 18. The forward or free end of the air purge head 27 is inserted between the respective adjacent rollers 4a, 4a in a state approaching the surface of the slab A at a distance of several millimeters. Where a narrow beam has a cross sectional area measuring, for example, 20 to 50 mm×500 mm, a size larger than the area of the opening of the forward end of the air purge head 27 measuring, for example, 15 mm in height and 500 mm in width, then the cross sectional area of the narrow light beam is restricted to that of the opening of the air purge head 27. As a result, a light beam emitted on the surface of the slab A always has a fixed cross sectional area.

Figure 4:
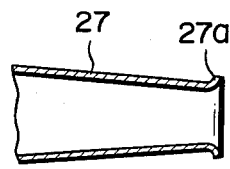
FIG. 4 is an enlarged sectional view of the outer end portion of an air purge head.

The free end of the air purge head 27 is bent outward all around with a curvature radius of 1 to 10 mm, as shown in FIG. 4, substantially to constitute a flange 27a. This flange section 27a is a means for preventing the air purge head 27, more particularly its free end portion, from being thermally deformed during the operation of a continuous casting plant. Any other means than the flange 27a may be devised for reinforcement of the air purge head 27. Since the opening of the air purge head 27 sustains its original shape for a very long time, a light path between the light emitter 10 and the light detector 11 is little obstructed. Further, air streams easily flow through the opening of the air purge head 27, preventing the air purge effect from being decreased.

The air purge head 27 is made detachable from the purge hood body 26. Where, therefore, the air purge head 27 is considerably deformed by heat, the whole air purge hood 18 need not be thrown away, but the difficulty can be resolved simply by replacing the air purge head 27. The plane or surface shape of the air purge hood 18 is made progressively broader as it is extended from the housing 17 to the roller 4a (see FIG. 3). Therefore, the lateral length of a flange 28 for connecting the air purge hood body 26 to the air purge head 27 is made shorter than the maximum width L (FIG. 3) of said air purge head 27 measured at its forward end. Where, therefore, a plurality of air purge hoods 18 are arranged side by side along the width of a slab A, then the flanges 28 of the respective adjacent purge hoods 18 are prevented from being touched by each other. The above-mentioned arrangement helps the openings of the air purge hoods 18 to be lightly set side by side across the slab A.

With the subject strip surface-examining apparatus constructed as described above, the housing 17 and that side of the air purge hood body 26 which faces the housing 17 are forcefully cooled with water, thereby decreasing the interior temperature of the housing 17, and obstructing heat transfer from the air purge head 27 to the housing 17.

In FIGS. 2 and 3, reference numeral 29 denotes a gas pipe; 30 an electric wire; and 31 a cooling water pipe. The housing 17 is filled with compressed inert gas, for example, nitrogen gas through the gas pipe 29, thereby preventing external air from being carried into the housing through a leak. A transparent glass plate 41 is hermetically sealed in the base portion of the air purge hood body 26 to act as a partition wall for separating the air purge hood region from the housing region. As a result, the interior of the housing 17 is rendered airtight. Further, the interior of the air purge hood 18 is also rendered airtight except for the opening of the air purge hood head 27. Accordingly, purge air entering the air purge hood 18 through the air pipe 40 is naturally ejected from the opening of the air purge hood head 27, thus improving the air purge effect. The partition wall 41 made of transparent glass does not obstruct a light path at all. Where cooling water happens to enter the air purge head 27 through its opening while the subject strip surface-examining apparatus remains inoperative, the glass partition wall 41 prevents the water from being further carried into the housing 17. Connected to the aforesaid cooling water pipe 31 is a forced water-cooling pipe (not shown) which is so arranged as to surround the light emitter 10.

According to this embodiment of the invention, a plurality of units each consisting of the light emitter 10, light detector 11 and air purge device 12 constructed as previously described and constituting the main part of the subject strip surface-examining apparatus are set side by side across the surface of the slab A. According to said embodiment, the slab A is chosen to be 2000 mm wide, and the lateral length L of the opening of the air purge head 27 is made to measure 500 mm. Accordingly, four strip surface-examining units of the light emitter 10, light detector 11 and air purge device 12 can be set side by side across the surface of the slab A, thereby making it possible to photograph the surface condition of the entire width of the slab A. Further, it is possible to broaden a single air purge hood 18 to cover the entire width of the slab A and set a plurality of light emitters 10 and light detectors 11 inside said air purge hood 18, thereby causing the end portions of patterns of light beams received by the respective adjacent light detectors 11 to overlap each other with no gaps left over therebetween and more favourably examining the crosswise surface of a steel strip with greater accuracy.

Figure 5:
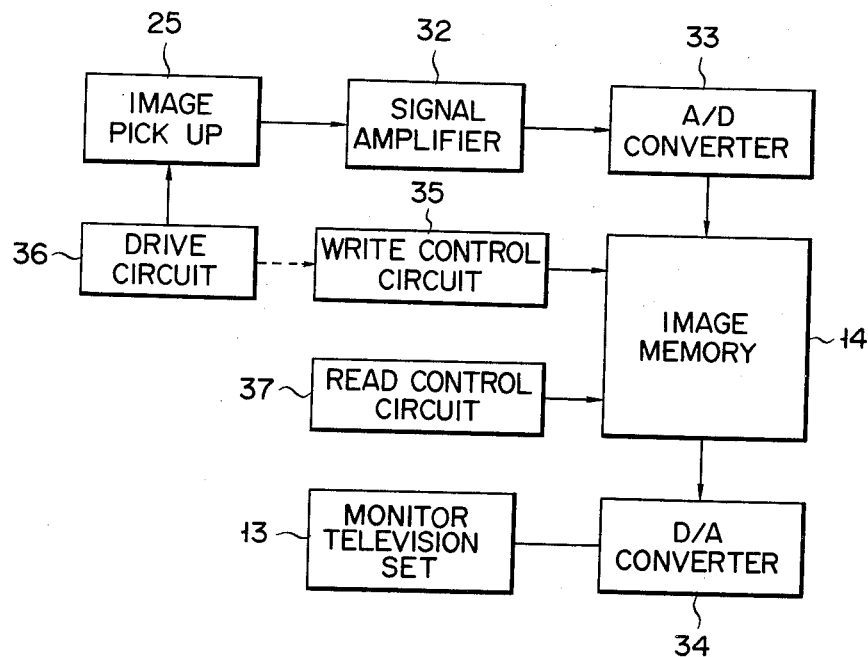
FIG. 5 is a block circuit diagram of an image-producing circuit constituting part of the surface-examining apparatus of the invention.

The image memory 14 is formed of, for example, a scan converter, magnetic memory or digital IC memory. It is particularly preferred to use a digital IC memory. The digital IC memory can store quantized display data corresponding to the screen size of the monitor television set 13. This digital IC memory is a stack-like assembly of memory planes capable of storing data corresponding to an extremely large number of addresses arrived at by multiplying 512 bits arranged in a vertical row and 512 bits arranged in a horizontal row. Said memory plane can store light and dark picture elements each consisting of 4 bits. An image-producing circuit whose main section is constituted by said image memory 14 is arranged as shown in FIG. 5. This image-producing circuit comprises an amplifier 32 for amplifying signals delivered from the image pickup 25; an analog-digital (A/D) converter 33 for converting an amplified analog signal into a digital signal and supplying said converted digital signal to the image memory 14; a digital-analog (D/A) converter 34 for converting a digital picture element signal read out of the image memory 14 into an analog signal, and conducting said converted analog signal to the monitor television set 13; a write control circuit 35 designed to cause image data (address data and data on light and dark picture elements) to be stored in the image memory 14, and control said write operation upon receipt of a synchronization signal issued from the drive circuit 36 for driving the image pickup 25; and a read control circuit 37 for causing image data to be successively read out of the image memory 14. Upon completion of the scanning of the image pickup 25 and by means of a scrolling process, the image-producing circuit indicates on the monitor television set 13 an image of the same pattern as that which is obtained when an ordinary television camera is applied as an image pickup. The monitor television set 13 used with the strip surface-examining apparatus of this invention has a screen measuring, for example, 375 mm in the vertical direction and 500 mm in the horizontal direction.

Figure 6:
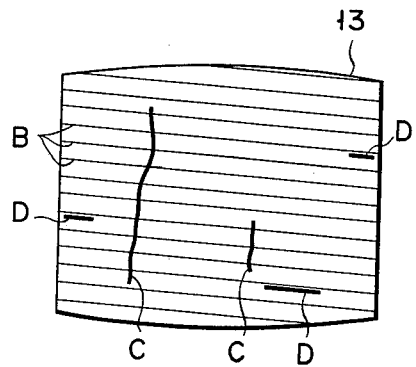
FIG. 6 is a front view of a picture appearing on a monitor television set when scarfs are detected on the surface of a steel strip in the process of being continuously cast.

There will now be described the operation of the subject strip surface-examining apparatus. The light emitter 10 projects narrow light beams of short wavelength or other narrow light beams containing those of such short wavelength on the surface of a slab A in the process of being continuously cast. Among the reflections of said projected light beams and light beams sent forth from the hot slab A itself, only blue light beams of short wavelength are detected by the light detector 11 provided with the filter 23. Observation is made of that limited section of the surface of the slab A on which the above-mentioned narrow light beams have been projected. The shadow of the slab A corresponding to said limited section is converted into electrical signals by the image pickup 25. After being amplified, the electrical signals are converted into digital form by means of the A/D converter 33. The converted digital signals are written in the image memory 14 upon receipt of an instruction issued from the write control circuit 35 operated jointly with the drive circuit 36 of the image pickup 25. The drive circuit 36 is conventional and supplies power clock pulses, start pulses, etc. to the image pickup 25, as required. Thus, image data denoting the surface condition of the slab A is successively stored in the image memory 14. Image data already stored in the image memory 14 is successively read out therefrom by the read control circuit 37 operated upon the scanning of the monitor television set 13. Output signals from the read control circuit 37 are supplied to the monitor television set 13 through the D/A converter 34. As illustrated in FIG. 6, image data thus read out is scanned in succession, to produce an image on the screen of the monitor television set 13. Though, therefore, a field of observation carried out at a point of time is based on narrow light beams, it is possible eventually to produce an image representing the broad (500 mm × 500 mm) surface area of the slab A. An operator sitting in an operation room 15 examines the surface condition of the slab A by watching indications on the screen of the monitor television set 13. When detecting a scarf, the operator supplies data on the size and position of the scarf to, for example, a computer by operating a keyboard. As produced on the monitor television set 13 (FIG. 6), scarfs C intersecting the oscillation marks B and scarfs D lying parallel with said oscillation marks B are indicated in black so as to be easily observed by an operator. In this case, the condition of the surface of the slab A having an area of 500 mm × 500 mm is projected on the screen of the monitor television set 13. Therefore, vertical scarfs mostly measuring 50 to 300 mm in length are indicated on the screen of the monitor television set 13 without interruption and moreover in an easily visible form. Since the scarfs remain on the screen for a relatively long length of time, an operator can fully recognize the scarfs without much mental tiring. Where it is attempted by the prior art examination method to project the condition of the surface of a slab A on the screen of the monitor television set 13, then not only portions of the surface of the slab A but also the shadows of, for example, four rollers 4a themselves are displayed on the screen of the monitor television set 13. The shadows of the rollers 4a occupy considerable portions of the screen of the monitor television set 13, causing vertical scarfs in particular to be restrictively recognized through the gaps between the rollers 4a. This obviously presents difficulties in observation and makes it impossible to determine the length of the vertical scarfs. Therefore, the conventional strip surface-examining method is not adapted for practical detection of scarfs. As is apparent from the foregoing description, the image-producing circuit of this invention (FIG. 5) provided with the image memory 14 enables the condition of the broad surface area of a slab A to be indicated on the screen of the monitor television set 13 without being obstructed by the shadows of the rollers 4a as previously described. According to the foregoing embodiment of this invention, therefore, it is possible to provide a strip surface-examining unit comprising the light emitter 10, light detector 11 and air purge device 12 even where a plurality of rollers 4a are arranged in parallel on both sides of a traveling slab A with the linearly adjacent ones of said rollers 4a spaced from each other at a small distance. Needless to say, the above-mentioned unit can be set in a broader space between the respective linearly arranged rollers 4a for examination of the surface condition of the traveling slab A. The lower compartment 9a of the air chamber 9 in which there is set the above-mentioned strip surface-examining unit comprised of the members 10, 11, 12 is wetted with sprayed water and also densely filled with steam. However, the air purge hood 18 protects the light emitter 10 and light detector 11 from falling water particles. Further, air streams passing through the air purge hood 18 at a pressure of several atmospheric units (preferably 5 atmospheres) purge water, steam and scales dropping off a traveling slab A from the light paths of the light emitter 10 and light detector 11, thereby ensuring the proper functioning of those elements. Therefore, the surface condition of a traveling slab A can be reliably examined even under the above-mentioned unfavourable condition. When set in the positions of E to H (FIG. 1) outside of the cooling chamber 9 which are environmentally more favoured than the cooling chamber 9, particularly the lower compartment 9a thereof, then the strip surface-examining unit comprised of the elements 10, 11, 12 can obviously function far better. This invention has the advantages that a compact strip surface-examining unit can be installed any where in a continuous casting plant to examine the surface condition of a traveling slab A by the joint action of the image-processing unit of the image-producing circuit and the air purge device; since the site of said strip surface-examining unit can be freely chosen, it is possible always to detect scarfs, regardless of the region of a continuous casting plant in which they occur; determination of the frequency of the respective forms of scarfs is ensured, thereby greatly contributing to the search for causes of the appearance of scarfs on the surface of a steel strip while it is continuously cast and consequently the improvement of the technique of operating said continuous casting plant.

The air purge hood 18 which is cooled not only by air strems but also forcefully by water prevents the light emitter 10 and light detector 11 from being disabled by the heat which might otherwise be transmitted to said elements 10, 11 from the air purge head 27 always heated by heat rays reflected from the slab A. As previously mentioned, the air purge hood 18 is formed of a hood body 26 and air purge head 27. If, therefore, the air purge head 27 is thermally damaged or deformed, the difficulty can be easily resolved by simply replacing the defective air purge head 27 with a new one. This means that the light emitter 10 and light detector 11 always have a fixed position relative to a traveling slab A, a favourable factor for operation of a continuous casting plant.

According to the foregoing embodiment, the surface condition of a slab A can be effectively examined in the cooling chamber 9, that is, in a considerably early stage of continuous casting after the withdrawal of the slab A from the casting mold 3. If, in case scarfs are detected, a signal denoting said detection is supplied, for example, to a control operator of a continuous casting plant, then it is possible early to take counter-measures for at least one of the conceivable causes for the growth of scarfs, for example, adjustment of the casting rate of a steel strip. Further, it is possible to control the position, and operation of a hot scarfer and the volume of gas used at a proper point of time in accordance with a signal delivered from a keyboard, thereby removing scarfs produced on the surface of the steel strip.

This invention is applicable not only to the above-mentioned curved strip type continuous casting plant, but also to a vertical slab or billet type continuous casting plant. Further, the casting whose surface condition is examined by the examining apparatus of the invention obviously includes not only steel but also any other metals.

As described above, the method and apparatus of this invention for examining the surface of a continuously cast steel strip for detection of scarfs appearing thereon have the advantages that the surface of said continuously cast steel strip can be examined for detection of scarfs, if any, produced thereon accurately and safely by a remote contactless control process, thereby greatly contributing to the progress of the engineering of continuous casting; a signal denoting the detection of scarfs is supplied to a control room early to enable measures to be taken for suppressing the growth of scarfs, thereby ensuring an increase in the yield and an improvement in the quality of a cast steel strip due to the accurate reliable detection of surface scarfs; it is unnecessary to cool a cast steel strip to room temperature and reheat said strip after removing its surface scarfs, as is the case with the prior art strip surface-examining method, thereby saving heat and shortening the time required for examining the surface of the strip; an air purge device provided with an air purge hood reliably purges the environment of a light path extending between a light emitter and light detector, thereby making it possible to set the subject strip surface-examining apparatus even in such a location as a cooling chamber which is environmentally less favoured; the air purge device, light emitter and light detector can be assembled into a compact unit, making the subject strip surface-examining apparatus easy to handle; the surface of a cast steel strip can be effectively examined by disposing of, for example, scales peeling off a cast steel strip without the necessity of installing such equipment as a cyclone dust collector; and when the detachably fitted air purge head is thermally damaged or deformed, the difficulty can be easily resolved simply by replacing the defective air purge head by a new one.

What we claim is:

1. In a continuous casting process for making metal strips, a method for examining the surface of a traveling metal strip during the continuous casting process for detection of scarfs produced on said surface, comprising positioning a light emitter having a light source and a light detector to face the traveling metal strip; projecting light beams from the light emitter on the traveling metal strip; receiving in the light detector light beams which are reflections of said projected light beams from the traveling metal strip and generating signals from the light detector which are a function of the received reflected light beams, thereby producing a shade image of the traveling metal strip; and detecting scarfs, if any, appearing on the surface of the metal strip in accordance with the contents of said signals generated by the light detector;

the improvement wherein:
the light source of the light emitter emits light beams of short wavelengths and also other waves;
projecting the light beams across the metal strip in the form of narrow bands;
filtering the reflections of said projected light beams so that only those light beams which consist of said short wavelengths are received by the light detector;

air purging a light path extending between the light emitter and light detector to prevent contamination from getting into the light paths between the light emitter and the light detector; and processing said signals generated by the light detector by an image memory system continuously to produce the shade image of the metal strip on a monitor television set.

2. The method of claim 1, comprising projecting the light beams from the light emitter onto the metal strip at a slight angle of inclination to the normal to said metal strip in its traveling direction.

3. The method of claim 1, wherein the casting process includes passing the metal strip through linearly adjacent support rollers set in a cooling chamber, the method further comprising projecting the light beams from the light emitter onto the metal strip through a space between the respective linearly adjacent support rollers set in said cooling chamber.

4. The method according to claim 1, wherein the air-purging step includes air-purging a region including said light path by introducing air streams into said region at a pressure of substantially 5 atmospheres.

5. The method of claim 1, comprising locating a further light emitter adjacent the first-mentioned light emitter; and delivering light beams, where necessary, from said further light emitter to the metal strip, the reflections of which are received by the light detector.

6. In an apparatus for examining the surface of a traveling metal strip in a continuous casting apparatus for detection of scarfs produced on said metal strip surface, comprising a light emitter provided with a light source and disposed to face said traveling metal strip; a light detector facing said traveling metal strip for receiving reflections of light beams projected by the light emitter onto the metal strip, the light detector generating electrical signals which are a function of the received reflected light beams; and processing means coupled to said light detector for electrically processing said signals generated by the light detector;

the improvement wherein:

the light emitter includes a light source which produces light beams of short wavelength and also other waves;

means is provided for projecting said light beams onto the metal strip and across the metal strip in the form of narrow bands;

said light detector includes a filter which passes only light beams of said short wavelengths selected from the reflections of said projected light beams;

air purge means is provided for air-purge cleaning the environment of the light paths of said light emitter and said light detector, said air purge means including an air purge hood surrounding the light path extending between the light emitter and light detector to air-purge the environment of said light paths; and said processing means includes an image memory for storing image data which corresponds to image signals supplied from the light detector, an image-producing circuit coupled to said image memory for causing image data to be written therein and read out therefrom, and a monitor television set coupled to said image-producing circuit and on which the surface condition of the metal strip is displayed in accordance with the contents of signals issued from said image-producing circuit.

7. The apparatus of claim 6, wherein said continuous casting apparatus includes a cooling chamber in which are located a plurality of linearly adjacent support rollers through which the metal strip is drawn; said air purge means is received in the cooling chamber; said air purge hood has a free end portion which is inserted between respective linearly adjacent rollers.

8. The apparatus of claim 7, wherein said air purge hood includes an air purge hood body and air purge hood head having a base portion which is detachably fitted to said air purge hood body, said air purge hood head having a free end which is opened close to the metal strip.

9. The apparatus of claim 8, including thermal deformation-preventing means formed at the opened end of the air purge hood head to prevent thermal deformation of the air purge hood head.

10. The apparatus of claim 9, wherein the thermal deformation-preventing means comprises an outwardly bent flange formed at the peripheral edge of the opened end of the air purge hood head.

11. The apparatus of claim 6, wherein the air purge hood has a width progressively broadened toward the end thereof in the crosswise direction of the metal strip.

12. The apparatus of claim 6, comprising a further light emitter located adjacent said first-mentioned light emitter.

* * * * *